United States Patent
Riesinger

(10) Patent No.: US 10,327,955 B2
(45) Date of Patent: Jun. 25, 2019

(54) ABSORBENT ARTICLE FOR APPLICATION TO HUMAN OR ANIMAL SKIN SURFACES

(71) Applicant: BSN medical GmbH, Hamburg (DE)

(72) Inventor: Birgit Riesinger, Munster (DE)

(73) Assignee: BSN medical GmbH, Hamburg (DE)

( * ) Notice: Subject to any disclaimer, the term of this patent is extended or adjusted under 35 U.S.C. 154(b) by 568 days.

(21) Appl. No.: 14/262,540

(22) Filed: Apr. 25, 2014

(65) Prior Publication Data

US 2014/0316353 A1 Oct. 23, 2014

Related U.S. Application Data

(62) Division of application No. 12/091,969, filed as application No. PCT/EP2006/010482 on Oct. 31, 2006, now Pat. No. 10,166,147.

(30) Foreign Application Priority Data

Nov. 2, 2005 (DE) .......................... 20 2005 017211

(51) Int. Cl.
 *A61F 13/00* (2006.01)
 *A61F 13/06* (2006.01)

(52) U.S. Cl.
 CPC .. *A61F 13/00063* (2013.01); *A61F 13/00008* (2013.01); *A61F 13/00029* (2013.01);
 (Continued)

(58) Field of Classification Search
 CPC .... A61F 2013/0054; A61F 2013/00536; A61F 13/00; A61F 13/02; A61F 13/0243;
 (Continued)

(56) References Cited

U.S. PATENT DOCUMENTS

| | | | |
|---|---|---|---|
| 3,669,103 A | * | 6/1972 | Harper .................... A61L 15/60 526/264 |
| 4,820,293 A | | 4/1989 | Kamme |

(Continued)

FOREIGN PATENT DOCUMENTS

| | | |
|---|---|---|
| DE | 4338326 A1 | 5/1995 |
| DE | 69323398 T2 | 8/1999 |

(Continued)

OTHER PUBLICATIONS

Advisory Action issued in corresponding U.S. patent application, pp. 1-4 (dated Jun. 9, 2015).

(Continued)

*Primary Examiner* — Ophelia A Hawthorne
(74) *Attorney, Agent, or Firm* — Rankin, Hill & Clark LLP

(57) ABSTRACT

The invention relates to an absorbent article for application to human or animal skin surfaces in the region of wounds, consisting of an outer covering (2) which is permeable for liquid substances, and of an inner layer (1) which is surrounded by the covering (2) and which consists essentially of a mixture of an amount of strongly osmotically active substances with an amount of osmotically comparatively weak or osmotically inactive substances, such as cellulose. The inner layer (1) is filled with osmotically active substances in such a way that it is possible to exert on a wound, with the wound fluids contained therein, an osmotic pressure via which the wound fluid can be removed from the organism to be treated, and thus it is possible to assist both in the surfaced wound region and in the depth of the tissue a normal interstitial hydration of tissue by directing endogenous fluids in their direction of flow to the patient's skin surface into the absorbent article, and keeping them there.

20 Claims, 4 Drawing Sheets

(52) U.S. Cl.
CPC ...... *A61F 13/00068* (2013.01); *A61F 13/069* (2013.01); *A61F 2013/0054* (2013.01); *A61F 2013/0074* (2013.01); *A61F 2013/0091* (2013.01); *A61F 2013/00157* (2013.01); *A61F 2013/00229* (2013.01); *A61F 2013/00519* (2013.01); *A61F 2013/00748* (2013.01)

(58) Field of Classification Search
CPC .......... A61F 13/00063; A61F 13/00008; A61F 13/00029; A61F 13/15203; A61F 13/53; A61F 13/511; A61L 15/60
See application file for complete search history.

(56) References Cited

U.S. PATENT DOCUMENTS

| | | | |
|---|---|---|---|
| 4,829,293 A | 5/1989 | Schlater | |
| 5,082,723 A | 1/1992 | Gross et al. | |
| 5,250,043 A | 10/1993 | Castellana et al. | 604/336 |
| 5,350,370 A | 9/1994 | Jackson et al. | |
| 5,397,316 A | 3/1995 | LaVon et al. | |
| 5,505,718 A | 4/1996 | Roe et al. | 604/368 |
| 5,681,579 A | 10/1997 | Freeman | 424/448 |
| 5,728,085 A * | 3/1998 | Widlund | A61F 13/2051 162/289 |
| 5,998,032 A | 12/1999 | Hansen et al. | 428/403 |
| 6,169,223 B1 | 1/2001 | Mahr et al. | |
| 6,191,335 B1 | 2/2001 | Robinson | |
| 7,714,183 B2 | 5/2010 | Caskey | 602/48 |
| 7,858,841 B2 * | 12/2010 | Krautkramer | A61F 13/531 604/359 |
| 2003/0120249 A1 | 6/2003 | Wulz et al. | |
| 2003/0229326 A1 | 12/2003 | Hovis et al. | 604/370 |
| 2004/0122389 A1 | 6/2004 | Mace et al. | |
| 2004/0137190 A1 | 7/2004 | Lasko | 428/90 |
| 2005/0175579 A1 | 8/2005 | Koganov | |
| 2006/0036222 A1 * | 2/2006 | Cohen | A61L 15/18 604/360 |
| 2007/0020318 A1 * | 1/2007 | Silcock | A61L 15/28 424/445 |
| 2007/0225663 A1 * | 9/2007 | Watt | A61M 1/0088 604/313 |
| 2008/0004559 A1 | 1/2008 | Riesinger | 602/46 |

FOREIGN PATENT DOCUMENTS

| | | | |
|---|---|---|---|
| DE | 20118880 | 1/2002 | ............ A61L 15/24 |
| DE | 10250848 | 5/2004 | ............ A61F 13/02 |
| DE | 69822789 T2 | 3/2005 | |
| DE | 202005001562 U1 | 4/2005 | |
| DE | 202004017052 | 6/2005 | ............ A61M 1/08 |
| DE | 69826484 | 9/2005 | ............ A61L 15/00 |
| DE | 10059439 | 12/2005 | ............ A61F 5/44 |
| DE | 102004063599 | 7/2006 | ............ A61F 13/02 |
| DE | 202006007877 | 7/2006 | ............ A61F 13/00 |
| DE | 202005017211.1 | 11/2006 | |
| EP | 0358412 A2 | 3/1990 | |
| EP | 0 413 251 | 2/1991 | ............ A61F 13/02 |
| EP | 1 656 914 | 5/2006 | ............ A61F 13/00 |
| EP | 1942851 A1 | 7/2008 | |
| EP | 2359784 A1 | 8/2011 | |
| EP | 2537494 A1 | 12/2012 | |
| WO | 9001913 A1 | 3/1990 | |
| WO | 9111206 A | 8/1991 | |
| WO | 9200108 A1 | 1/1992 | |
| WO | 9509014 A1 | 4/1995 | |
| WO | 9828013 A2 | 7/1998 | |
| WO | 9831402 A2 | 7/1998 | |
| WO | 9831858 A2 | 7/1998 | |
| WO | 0056283 | 9/2000 | |
| WO | 0112902 A1 | 2/2001 | |
| WO | 0152780 A1 | 7/2001 | |
| WO | WO 2001/52780 | 7/2001 | ............ A61F 5/44 |
| WO | 0154641 A1 | 8/2001 | |
| WO | 035051410 A1 | 6/2003 | |
| WO | 03094813 A1 | 11/2003 | |
| WO | 2007051599 A1 | 5/2007 | |
| WO | WO 2007/085396 | 8/2007 | ............ A61F 13/00 |

OTHER PUBLICATIONS

Third Party Observations filed in corresponding foreign application, pp. 1-51 (Aug. 11, 2014).
Brockhaus Enzyklopädie: Neunzehnter Band TRIF-WAL, 1974, p. 442-445, F .A. Brockhaus Wiesbaden, Germany.
Cutting, Keith, "Wound exudate: composition and functions," British Journal of Community Nursing, Feb. 2003, p. 4-9, ResearchGate, Germany.
"Determination of the water absorption capacity of textile fabrics—DIN 53 923", Jan. 1978, Technical Standards Committee Material Testing in DIN German Institute for Standardization e.V. Textile Standards Committee Textiles and Textile Machines, Germany.
"Favor: Our superabsorber for modem hygiene products," p. 1-24, Evonik Industries, Germany.
Shell Atlas 2000/2001, p. 691.
Terrill, P. et al. "Absorption of blood by moist wound healing dressings," Primary Intention, Feb. 2003 p. 7-17, vol. 11 No. 1, Britannica.com.
"Cellulose", Wikipedia, p. 1-9, "Retrieved from https://en.wikipedia.org/w/index.php?title=Cellulose&oldid=971457008", Wikimedia Foundation, Inc.
Notice of Opposition for Lohmann & Rauscher GmbH & Co. KG dated Jun. 26, 2018 for the corresponding European Patent No. 2 359 784 B1.
Notice of Opposition for Paul Hartmann AG dated Jun. 26, 2018 for the corresponding European Patent No. 2 359 784 B1.
Notice of Opposition for Absorbest AB dated Jun. 27, 2018 for the corresponding European Patent. No. 2 359 784 B1; English translation.
Smola, Hans et al., "Polyacrylate-Superabsorber Inhibits Excessive Metalloprotease Activity in Wound Fluid from Non-healing Wounds," Wound Repair and Regeneration, Sep. 13-16, 2006, Abstract No. 31, p. A101, 16th Annual Meeting European Tissue Repair Society, Pisa, Italy; Cited in Hartmann Opposition.
Delivery note to Steripolar Oy, Espoo, Finland, dated Oct. 3, 2005; Cited in Absorbest Opposition.
Invoice to Steripolar Oy, Espoo, Finland, dated Oct. 6, 2005; Cited in Absorbest Opposition.
Delivery noted to Kirudan A/S, Brøndby, Denmark, dated Oct. 5, 2005; Cited in Absorbest Opposition.
Invoice to Kirudan A/S, Brøndby, Denmark, dated Oct. 5, 2005; Cited in Absorbest Opposition.
Certificate of Registration, Medical Products Agency, dated Sep. 6, 2005; Cited in Absorbest Opposition.
Product information to Medical Products Agency in Swedish, date of receipt Mar. 31, 2005; English translation; Cited in. Absorbest Opposition.
Application for registration to Medical Products Agency in Swedish, date of dispatch Mar. 30, 2005; partial English translation; Cited in Absorbest Opposition.
Declaration from Lena Jonsson regarding the features of the public prior used products F20021 and F20041, dated Nov. 21, 2016; Cited in Absorbest Opposition.
Declaration from Rolf Rovaniemi regarding the employment of Lena Jonsson, dated Jun. 25, 2018; Cited in Absorbest Opposition.

* cited by examiner

ABSORBENT ARTICLE FOR APPLICATION TO HUMAN OR ANIMAL SKIN SURFACES

CROSS-REFERENCE TO RELATED APPLICATIONS

The present applications claims priority from and is a divisional of U.S. patent application Ser. No. 12/091,969, filed Jul. 31, 2008; which is U.S. National Stage Application from PCT Application No. PCT/EP2006/010482, filed Oct. 31, 2006, which claims priority from German Application No. 20 2005 017211.1, filed Nov. 2, 2005, all of which are herein incorporated by reference in their entireties.

BACKGROUND

The invention relates to an absorbent article for application to human or animal skin surfaces in the region of wounds, consisting of an outer covering which is permeable for liquid substances, and of an inner layer which is surrounded by the covering and which consists essentially of a mixture of an amount of strongly osmotically active substances with an amount of osmotically comparatively weak or osmotically inactive substances, such as cellulose.

An absorbent article of the type mentioned at the outset is revealed in the applicant's DE 100 59 439. The known absorbent article has proved very useful in practice, but there is a need to strengthen the absorption efficiency, especially for moderately to heavily discharging, infected wounds from which the wound exudate can be absorbed more efficiently from the depth of the wound floor.

This object is achieved by an absorbent article of the type in question in which the inner layer is filled with osmotically active substances in such a way that it is possible to exert on a wound, with the wound fluids contained therein, an osmotic pressure via which the wound fluid can be removed from the organism to be treated, and thus it is possible to assist both in the surfaced wound region and in the depth of the tissue a normal interstitial hydration of tissue by directing endogenous fluids in their direction of flow to the patient's skin surface into the absorbent article, and keeping them there.

The inner layer is designed in such a way that the mass per unit area is at least 420 g/m$^2$, with the mass per unit area of the proportion of osmotically active substances which is uniformly distributed therein being at least 200 g/m$^2$.

The concepts of treating chronic wounds and oedema therapy often cannot be separated, because inflammatory processes, infectious events and leaks from vessels occur with one type as well as the other.

If oedematous fluid resulting from pathological processes enters the cells of a tissue, these cells are compressed. Their distance from vessels which provide nourishment or transport away grows, diffusion processes become more difficult, metabolic products accumulate and oxygen becomes rare. An additional factor is that metabolic products escape from dying cells, so that sugar catabolites such as lactic acid (lactate from glycolysis) or else citric acid accumulate and bring about active breakdown of collagen and destroy tissues.

Theoretically, this breakdown of tissue, which is equivalent to the production of a wound, underlies a large number of further processes. Activated leucocytes, growth factors adhering to fibrin (growth factor trap hypothesis) and hypoxic areas assist the tissue breakdown.

The causes of the perturbing potency lie in the presence of hyperhydration and long residence times of water in tissue. A therapeutic approach taking account of this realization is vacuum therapy, in which the wound region is exposed to specific subatmospheric pressures by means of closed systems. The healing results are impressive.

The disadvantages are that this therapeutic approach is a very costly and elaborate procedure requiring apparatuses. It is therefore advantageous to apply analogous mechanisms following different physical laws to the wound region, for example by a dressing according to the invention with high osmotic subatmospheric pressure. Oversized amounts of water-storing polymers, e.g. 200 g/m$^2$, fulfil this task and are useful in that water molecules abandon contact with other water molecules only on application of a high separation force. The circumstance that a molecule as small as water must be heated up to 100° C. in order to achieve this separation proves this.

Accordingly, water molecules in deep layers of tissue are also reached, and the excess aqueous exudates there are sucked out, via the suction on water molecules located on the surface. Cohesive forces of the water permit chain-like removal of water molecules as far as the site of development of the oedemas.

This suction achieves a large number of advantages. Collagen-degrading substances such as citric acid or lactic acid which are present in the oedema and there actively maintain the wound are removed. Diffusion processes become easier again, the cells receive oxygen, building substances and mediators such as growth factors. Collagen synthesis can start.

By utilizing the unwanted exudate as carrier substance and as rinsing agent for the wound region, substances present in the exudate are rinsed through a plurality of tissue layers and cleanse the layers of the wound.

Known wound-contact materials with superabsorbent substances have the property of binding escaping water in order to avoid noticeable escape thereof. Although a "depth effect" is mentioned, it is not defined. By contrast, the present absorbent article achieves, for example with leg ulcer (VLE), a depth effect as far as the insufficient vein and thus as far as the perivenous tissue and its oedema. A swelling process in the absorbent article achieves adaptation to the wound floor in the sense of wound morphology adaptation because of the displaceability of the saturated superabsorbent granules.

The absorbent article may be present in a dressing as combination product. Additional pockets or coverings with perforated films in the sense of wound-distance lattices can be inserted into the absorbent article. It can also be used here adjacent to other dressing materials such as foam dressings, alginates, hydrophilic fibres, polyhexanides and carriers, CMC (carboxymethylcellulose), hydrophilic fibres, hydrocolloids, lipocolloids, honey, activated carbon, silver, cellulose, drugs, hydrogels, detergents such as surfactants and poloxamers and carriers thereof, other superabsorbent-containing articles or mixtures of such devices. Depending on the mode of use, the product can be placed with one side towards the wound, in which case the absorbent article has indirect contact with the wound; it can also be directed with the other type of dressing material towards the wound, in which case the type of dressing material forms a flow-through element through which the absorbent article draws the exudates and thus increases its absorption capacity and prolongs the time it is left on the wound.

The covering may consist of more than one film or cover, for example in such a way that a nonwoven is present on one side and a water-resistant or water vapour-permeable backsheet is present on the other side. Another possibility is to use a three-dimensionally shaped wound-distance lattice on one side and a cover with special functions such as the carrying of activated carbon or antiinfective agents on the other side. Two homogeneous covers or mixing of different covers are possible.

The covering consisting of one or more cut sections should preferably be bonded, ultrasonically welded, thermally generated or mechanically accomplished. The seam preferably does not form the outer edge of the product, but leaves an unsewn material portion which has uni- or multilamellarly flexible and soft product edges. This covering may be partly or entirely closed in the periphery, remain open on at least one length or have duplicatures.

Besides a spatial proximity of products next to the absorbent article within a covering, it is possible for the substances mentioned, such as foam dressings, alginates, hydrophilic fibres, polyhexanides and carriers, CMC, hydrocolloids, lipocolloids, honey, activated carbon, silver, cellulose, drugs, hydrogels, detergents such as surfactants and poloxamers and their carriers, other superabsorbent-containing articles or mixtures of such materials themselves to be present in the absorbent article, for example in such a way that the superabsorbent granules are incorporated into materials of this type, also in addition to other layers which comprise the superabsorbent particles or other osmotically active substances.

One embodiment would be incorporation of superabsorbent substances into hydrophilic fibres which are present as carrier substance therefor. It is possible for additional cover layers of other materials such as cellulose to be present within a covering of the inner layer, this product of superabsorbent substances, hydrophilic fibres, cellulose cover layer or cover layer made of hydrophilic fibres and covering is present in a second covering which additionally comprises at least one of the materials mentioned. This may also be present in this covering alone or adjacent to further materials in an additional covering, so that an interior and two or more coverings are present in the overall product. Intermediate layers may be disposed between these and may have a waterproof, water vapour-impermeable, air-permeable, semipermeable or other type of configuration.

One possibility for ensuring the dimensional stability is firm pressing of the aforementioned substances of the absorbent article, with adhesives not necessarily being required.

The result is a product which includes materials such as CMC, hydrophilic fibres, alginates or other substances of those mentioned in covered form, with the purpose of redrying other materials of the dressing by the osmotically more active materials such as granular superabsorbent substances, and therefore extending the useful life of these materials and their functioning and therefore saving costs, material and care time. In parallel, phases without disturbance of the wound are prolonged, stable temperature conditions in the wound, which is important for repair processes, are achieved, and there is a bilateral interaction of the flat sides of the materials. This is because, on the one hand, these materials act in known form beneficially in the direction of the wound on the wound region, whereas they experience redrying on their reverse side facing away from the wound due to other portions of the dressing material. The materials applied closer to the wound thus display their effect, and the opposite ones can bring about a flow-through rinsing through themselves into the other portions of the dressing material.

The superabsorbent substances, chiefly granules, can be pressed into or introduced into fibre mats, but can also be bonded in, welded or fixed in other ways. Two cover layers are able here to cover a mix of cellulose and superabsorbent substances which are produced for example as airlaid mat. The superabsorbent substances can, however, also be incorporated into all other known materials, especially into hydrocolloid fibres, alginates or a blend of different substances of the type mentioned or with third materials.

Two layers of cellulose with intermediate superabsorbing substances (without cellulose) as sandwich arrangement are likewise conceivable.

Since a change of dressing is associated with a reduction in the temperature of the wound region, it is conceivable to supply the absorbent article with reagents which keep the wound temperature stable in the sense of a controlled, biocompatible, exothermic reaction. Chemical reactions such as processes based on pepper can be taken into account, especially because these will also set up an additional osmotic suction.

The product can be used as part of a compression therapy, dressing as part of a therapy for compartmental syndrome or in vacuum therapy by means of subatmospheric pressure. In the latter case, the two types of pressure, subatmospheric and osmotic, are added together so that a very sufficient oedema therapy results.

Known dressings with superabsorbent particles do not reach the necessary potency for several reasons. The known dressings' contents of superabsorbent substances are too low, and the potency of the latter is also artificially diminished because they are at a great distance from the wound region behind polyurethane foams or cellulose layers. In other products, the osmotic effect is weakened by solutions. Overall, the superabsorbent particles applied in this way have only very low osmotic potency, and their potential is exhausted within the dressing.

SUMMARY OF THE INVENTION

Provided herein are systems, methods and compositions for an Absorbent Element To Be Mounted On human Or animal Skin Surfaces.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

Exemplary embodiments of the invention are explained by means of the drawing. The figures show.

DETAILED DESCRIPTION OF THE INVENTION

Figure 1A:
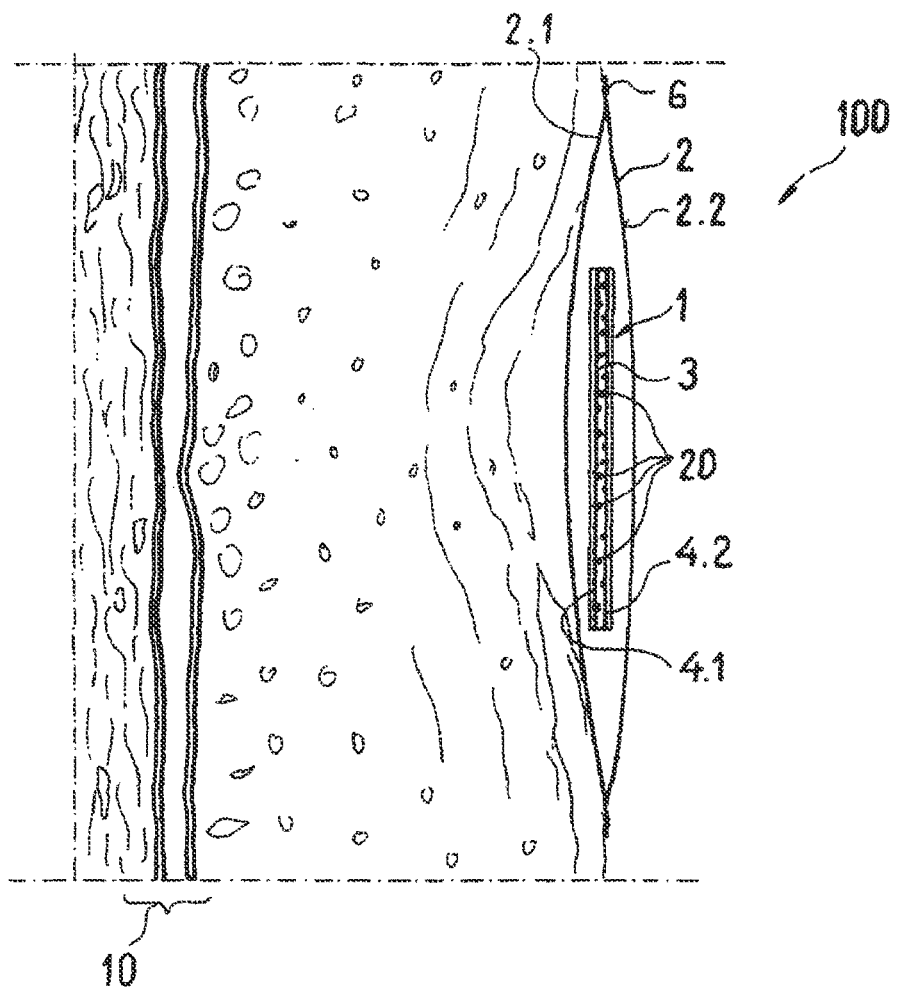
FIGS. 1a and 1b an absorbent article according to the invention employed in the therapy of leg ulcer, in diagrammatic representation.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

The absorbent article according to the invention is intended to be used for acute and chronic wounds, iatrogenic incisions in the skin, burn wounds, weeping inflammatory processes of the skin or ulcerative processes of neoplastic origin, weeping infections, fistulas, postoperative drains, stomata, atopically changeable areas of skin, skin duplicatures near joints, such as axillary or inguinal skin, mucocell surfaces of humans and animals, in conjunction with other dressing materials which have a local therapeutic effect and for other applications in which an atraumatic wound dressing is indicated. Split skin donor sites, plastic grafts, abscesses and urological applications may equally be fixed as indication, as well as proctological applications and prophylactic use for prevention, e.g. for controlling germ transmission and reducing the spread of germs. Functional combination with the other broadly described advantages is particularly important. Applications under subatmospheric pressure, whether continuous or intermittent, electrical or manual, applications in compression therapy or carbon dioxide bath form further essential possibilities.

Concerning the general understanding of the term "osmotically active" it should be noted:

The meanings are properties or totals of physical or/and chemical processes such as, for example, electronegativities, molecular masses, charge equalization, molecular interactions or dilution tendencies of substances such as salts, sugars and proteins, which owing to their own properties or amounts and concentrations bring about a pressure gradient in the sense of a tendency to flow or suck in for example aqueous substances.

Although the presence of a semipermeable membrane is necessary for experimental demonstration, the underlying laws take place at the molecular level even without the membrane.

Laws from the areas and topics of hypo-, iso- and hypertonia of individual components, diffusion, equalization processes and equalization energies, equilibria, hydrostatic pressure, osmotic pressure, chemical potentials, mixing effects, concentrations, molar density, entropy and Gibbs energy may be applied singly or cumulatively. Alternatively or in addition, rules relating to the processes of oncotic pressures, colloid-osmotically relevant processes and other events which are influenced by the number and/or nature of macromolecules may be present.

Described briefly, the processes applying here are preferably those leading to interactions with water, which direct and store this or at least enter into short-term connections therewith.

The meaning of this definition of direction of flow has far-reaching consequences. Examples which may be mentioned are:

Essentially two cleansing processes are carried out on the wound. Firstly, the superabsorbent particles remove the wound exudate from the base of the wound, thus supporting physiological normal hydration (normal fluid content). The edges of the wound are stabilized. The wound bed is positively conditioned. Secondly, secretions with a low water content are concentrated in front of the covering and adhere to the covering material and can be removed when the used absorbent article is changed.

The absorbent article according to the invention counteracts unwanted granulation of the wound. Since the pathological exudate is absorbed, harmful proteases, which include for example MMPs (matrix metallo proteases) and TIMPs (tissue inhibitors of metallo proteases), are sucked up. A secondarily antiinflammatory efficiency is achieved owing to active suction processes of the harmful proteases. The absorbent article adapts to the morphology of the wound region via the suction and swelling process.

The mat which is locally impregnated and swollen with wound fluid at least partly fills the respective wound.

The mat may initially be freely moveable within the covering.

Ideally, the swollen absorbent article is intended to lie on the whole area of the wound region. In this context, the covering wall facing away from the wound may consist of a textile or film material which is not stretchable or at least slightly stretchable, whereas the other wall near the wound is considerably more stretchable.

It is desired to maximize the surface area of the superabsorbent particles distributed in the core and to maximize the homogeneity of the core. The superabsorbent particles which are embedded in the core, preferably without adhesive, can form an essentially uniform matrix. It is possible in this context for the superabsorbent particles to have sharp edges so that their surface areas are enlarged. The sharp-edged superabsorbent particles at the same time improve the adhesion to the textile fibres which are preferably processed to give a random or directionally oriented, mechanically bonded web. The textile fibres may be kinked, curved or folded fibre sections differing in breadth and length. The textile fibres may at least partly run around the individual superabsorbent particles so that the interfaces and thus the suction force can be enlarged. Polymer fibres and natural fibres are suitable as textile fibres.

The superabsorbent particles may be for example cross-linked, partially neutralized acrylic acid polymers. The superabsorbent particles may also be gelatinous or ceramic.

It is possible to add to the superabsorbent particles a core crosslinker, in the present case as core crosslinker (CXL) or else as surface crosslinker (SXL), or a mixture of the two crosslinkers.

The absorbent article acts with such superabsorbent particles as hydroactive wound dressing which allows the absorbed fluid to evaporate again.

The possible uses of the absorbent article can be extended by adding pharmacological substances on an atomic or elemental basis, such as compounds with Zn, Ca, Na. The pharmacological substances include for example antiinflammatory agents, antibiotics, growth factors, homeopathic remedies, analgesics, antipyretics and disinfectants.

It is possible to add to the inner layer present in the covering, and/or to the covering, extracts of brown algae, carboxymethylcellulose, alginates, hydro-capillary, hydrogels, enzymes, compounds based on ceramic, growth factors, metallic additions, for example based on silver, gold, platinum and titanium, furthermore osmotically active substances such as salts, sugars, proteins, enzymes such as peroxidase, to control the osmotic pressure. It is possible to provide for addition of substances which reduce the germ count, such as octenidine and polyhexamide.

The pharmacological substances may be taken up and dissolved in part by endogenous fluids such as pathological wound exudate without the use of electrolyte solution.

Thus, the risk of mutations, biofilms, resistances and infections is reduced, and the efficacy of antibiotic measures by pharmacological interventions is improved, by the reduction in the germ count by physical properties of the dressing material.

For example, an effect directed in the direction of the absorbent article is achieved on non-surface exudate, which effect alters the transport of the emerging amount and the rate of transport. The pathological tendency to a particularly slow flow of the wound fluids through the tissue, which may lead as far as stasis of the wound fluid in the depth of the tissue, leads to cellular oedema and hyperhydration of space between cells so that the stasis is moved in the direction of a flow of fluid to the absorbent article via the suction on the external exudate which is to be accomplished here. The hyperhydration of the depth of the wound floor is thus reduced, and its overall nutritional situation and thus its healing potential is improved.

Essentially two cleansing processes are carried out on the wound. Firstly, the superabsorbent particles remove the wound exudate from the base of the wound, thus supporting physiological normal hydration. The edges of the wound are stabilized and the wound bed is positively conditioned. Secondly, secretions with a low water content are concentrated in front of the covering and adhere to the covering material and can be removed when the used absorbent article is changed. The absorbent article according to the invention counteracts excessive granulation of the wound. Since the pathological exudate is absorbed, harmful proteases, which include for example MMPs (matrix metallo-proteases) and TIMPs (tissue inhibitors of metallo-proteases), are sucked up. A secondarily antiinflammatory efficiency is achieved owing to active suction processes of the harmful proteases. The absorbent article adapts to the morphology of the wound region via the suction and swelling process.

The absorption process may lead to the absorbent article becoming so heavy that it retards excessive granulation through its own weight and thus works towards wound bed homogenization. The weight-determining element is the wound exudate itself.

The result is thus a dressing material which, viewed superficially, has a homogeneous surface but, owing to its technical conception, provides a wound phase-specific general response.

An additional factor is that necrotic areas of the wound are scraped off and detached by the dressing material, with the subsequent weeping being trapped by the dressing material.

When a wound is infected, the absorbent article absorbs the germs and removes the germs, the toxins, the exudate, the sources of inflammation and the oedema from the wound. Since the oedema and parts of the inflammatory reaction assist the development of organized germ systems, called biofilm, the absorbent article shortens the duration of the infection, reduces the probability of the occurrence of the infection and acts synergistically with further antiinfective measures. The extent or the up germs such as MRSA (methicillin resistant *Staphylococcus aureus*) are controlled. Especially in the ambulant, domestic, non-inpatient sector, eradication of these population-endangering germs leads to a rapid healing of chronic wounds because only here do they find their pathogenic conditions and lead to possibly life-threatening, often uncontrollable infections. This also applies to germs such as VRE (vancomycin resistant *enterococci*) and CA-MRSA (community acquired MRSA).

When a wound is in the cleansing phase, the absorbent article actively absorbs the fluids which are rinsed out and firmly binds them. When a wound granulates, and new cells form, the absorbent article protects them from the composition of the pathological exudate of the wound region of the vicinity.

Where a wound is hypergranulating, the absorbent article retards it into the desired growth rate through its own weight and the weight of the absorbed exudation. The edge of the wound is kept free of inflammatory oedematous processes of the healthy skin.

Even where there is healthy tissue, the small thickness of the absorbent article under compression dressings contributes to transition edges of the dressing not being forced very deeply into the patient's skin, whereas many other products are rather thicker, and compressions or constrictions, squeezings or indentations or persistent pressure edges with the risk of decreases in perfusion arise and thus promote skin damage.

Compressive forces of surrounding compression dressings are transmitted unimpeded, whereas, following La Place's law, thicker dressings with the same compression surroundings and thus a greater radius impede compression in the depth and transmit less or even uncontrolledly less compression. This is the case in particular with foam dressings and thick cellulose layers because their elasticity further exacerbate this reduction here.

The absorbent article according to the invention can also be used for moist therapy without being wet from the outset.

It is possible for a significantly larger amount of comparatively small, rapidly absorbing superabsorbent particles to be present at a selected site of the absorbent article or the inner layer than elsewhere so that the function of a wound filler arises locally during the absorption process. If a wound-filling function is desired, an appropriate covering has walls differing in elasticity. The wall near the wound can in particular have a greater elasticity than the opposite wall facing away from the wound.

The absorbent article can furthermore have an underlay of at least one foam material layer which is attached by at least one adhesive point or a peripheral seam to the covering. The foam material layer may have open or closed pores and be hydrophilic or hydrophobic. If a foam material with closed pores is employed it is advisable to introduce continuous orifices in the foam material.

Otherwise, the continuous orifices or perforations can be introduced on any flat material which is a constituent of the absorbent article.

Possible addition of surfactants leads to a significant increase in the exudation of a wound and may be desirable. Materials which are in particular biocompatible and systemically and locally unobjectionable should be employed here, in order not to interfere with the complex cascades of interactions of pressure situations, perfusion, venous removal, cellular metabolism, motility and inertness of cells such as erythrocytes and granulocytes, of endogenous or added growth factors, immunorelevant cells and substances or other factors important for the growth of tissue. Possible vasodilatation in the wound region may have beneficial effects here, even if it is the result of addition of surfactants, because exudation of the wound region predominates here and the intention is for in-depth cleansing of the wound region. This also relates to the visually identifiable floor of the wound, the bottom of the wound which is relevant for causal therapy, and the edge of the wound, tissue parts which are to be protected from exudation and harmful substances through the superabsorbent granules or other wound-contact areas such as foams made of PU, PE or other polymers, cellulose, alginates, hydrogels, carbon compounds, silver preparations, honey, batts, nonwovens, antiseptics, carriers of the materials, films or fat-impregnated surfaces fulfilling this function.

These additions, like the surfactants, or other materials mentioned, may be attached covalently, detachably or freely on other surfaces.

Parts of the components may have different perforated structures which facilitate the interaction of superimposed layers. Penetration into the next layers in both directions, adding to and absorbing from the wound, is thus facilitated.

Further advantages can be achieved in combination with a foam dressing in a joint additional covering. Thus, two types of avoidance of disturbance of the wound are achieved:

When there is heavy exudation, the side which shows the absorbent article two-dimensionally in the covering is applied to the wound, and the absorbent article destresses the wound environment through the desired strong suction effect by removing therefrom the unwanted pathological exudate which includes harmful messengers and constituents. Interstitial and intercellular, but also cellular and also vascular, spaces approach a physiological hydration, so that perfusion, arterial inflow, venous removal and transmembrane diffusion are optimized and are not impeded by long diffusion pathways, by pathological aqueous solutions and reactive biorelevant enzymes. Cell growth requires the arterial inflow of proteins, oxygen as well as the insertion of vessels, nerves and bearers of immune defence functions.

When there is lighter exudation, the foam side of a foam dressing can be applied to the wound. The absorbent article here achieves an indirect factor of avoidance of disturbance of the wound by utilizing its suction force as redryer of the foam. For this it is necessary that the foam is almost completely wetted so that flow takes place through the foam, e.g. by capillary actions, and a gentle inflow into the absorbent article results. The absorbent article redries the foam here and forms a secondary reservoir which increases the capacity of the foam and the capacity of the absorbent article, with the latter having negligible contact with the wound itself.

A covering which surrounds the foam and the absorbent article in this embodiment can be formed from perforated PE film which has crater-like holes of the same or different geometry.

The principle according to the invention of the individual absorbent article makes it possible to carry out a visual, simplified check of the emerging wound exudate on use of such absorbent articles interspersed with superabsorbent particles, provided that the absorbent article is employed in the form of an appropriate size adapted to the wound.

It is a great advantage that the absorbed wound exudate can assume and maintain a limited position in the absorbent article, and thus the surrounding skin adjacent to the wound is not attacked by wound exudate.

To assist general understanding of the mode of functioning, it may also be emphasized:

A hyperhydration represents for example an oedema which develops on the basis of a CVI (chronic venous insufficiency). The vessel wall of the affected vein becomes more permeable owing to pathological processes, and non-negligible amounts of aqueous constituents which are initially present in the vein penetrate outwards into the space outside the vein. This takes place especially at the level of the ankle bone of the leg, because the blood column of the vein starts here and the hydrostatic pressure is greatest here.

Hyperhydration of the surroundings, of the healthy cells, of the skin and of the spaces between cells occurs. Diffusion of arterial and nutritionally important substances as well as the removal of used substances through the vein are impaired. The metabolic status of the cells is reduced, biorelevant processes and finely orchestrated metabolic cascades cease, and the cells die. A venous leg ulcer develops, breaks through to the skin and remains hyperhydrated for life.

The same process in the lung would be controlled by increasing renal output, at least if the whole lung were to be affected.

Using diuretics to control this hyperhydration in the lower leg is not indicated because there are a large number of medical reasons against this. This would result in an intervention in the cardiorelevant system complexes and since, in contrast to pulmonary oedema, there is no evident acute risk to life, other ways must be found.

In contrast to this knowledge, it is the practice in therapy to apply dressings of comparatively low suction force and deficient retention. The oedema in the leg tissue is in this case controlled in an undirected, passive, local and physical manner.

It is common to such therapeutic approaches that causal therapy (cardiac medication to strengthen the heart and therefore control the congestion of blood in the lung on the one hand and wearing of compression stockings to control the emergence of water expelled from the veins on the other hand) is combined with symptomatic treatment (diuresis to dehydrate the lung on the one hand as well as applying allegedly highly absorbent dressings on the other hand).

Whereas impairment of function of, for example, pulmonary tissue is categorized as threatening, the oedematous swelling of tissue near the joint is assessed as temporary and thus not a problem. The first imbalance arises here, and, although understandable in view of vital functions and maintenance of life, it underestimates the short route in patients' suffering, pain, chronic disorders, costs, sometimes also loss of employment and a large number of other disadvantages.

All medical professionals know that prescribed compression stockings are often not worn appropriately and perseveringly. It is evident here that the essential function of compressing leg tissue does not fit in with the patients' routine, because the donning, if in fact possible, is very troublesome and is regarded as very unpleasant. The patients perspire in summer, and removal is often difficult too.

As a result, either the prescribed compression stockings generate too little pressure, but are at least worn, or the stockings are not worn at all. The causal therapeutic approach involving for the lung increasing the cardiac output by medication often fails in the case of venous insufficiency because this can be achieved only by good compression therapy. If this does not take place ideally or at all, the vein will continue to discharge permanently.

Therapy with subatmospheric pressure systems, so-called vacuum therapy, appears to be more effective because this draws, by subatmospheric pressure conditions, on the depth of the point of emergence of fluids.

However, since this choice of therapy also has a large number of disadvantages which extend from high costs and immobility through high demands for application and even to deaths, it is necessary to find a third approach besides the nephrological-diuretic and besides the vacuum-assisted therapeutic approaches.

It would be advantageous in this context to have a dressing which can be applied simply and which makes use of known physical relationships and circumstances and dispenses with pharmacological processes.

According to the invention, a dressing which achieves the advantages of the subatmospheric approach without needing to combat the disadvantages of subatmospheric air pressure such as, for instance, the acquisition of air- and suction-tight chambers is chosen.

This is possible by the use of significant osmotic subatmospheric pressure conditions which are placed in the form of a dressing two-dimensionally on the wound surface and follow physical laws in a novel form.

The inner layer, which has the form of a mat of cellulose carrier material for superabsorbent particles, preferably has a mass per unit area of more than 300 g/m$^2$ and has more than 50% osmotically active substances. In one embodiment, the inner layer has a mass per unit area of at least 300 g/m$^2$, with the mass per unit area of the proportion of osmotically active substances which is uniformly dispersed therein being at least 100 g/m$^2$. The binding capacity is from 0.5 to 2 g of NaCl in 0.9% strength solution per g of the inner layer. The inner layer is configured such that absorbed liquid is only released if the inner layer becomes completely saturated.

Thus, the desired dressing places such a high osmotic potency (first force) in the wound that fluids of the wound surface are absorbed without delay. The cohesive forces thereof (second force) transmit this indication of the flow direction to adjacent wound fluids so that a depth effect results. A direction of flow of the excess wound fluids is therefore defined in the depth of the wound, and this is maintained and continued on the basis of several influences.

Besides the cohesive tendency of fluids, mention should also be made in this context of their adhesive tendency (third force) so that although only little fluid experiences the direct osmotic suction, indication of the direction thereof also reaches the depths. It is to be assumed that a mechanism (fourth force) based on capillary ascension also takes place between the cells in the depth of the tissue, so that maintenance of the definition of the direction of flow is assisted thereby.

The compressive force (fifth force), which is present in the depth, of the permeable vein supports this effect because it knows only the peripheral way out for the fluids towards the skin. The fifth influencing quantity which, prompted by the high osmotic suction, leads to a relief of the hyperhydration of the bottom of the wound would be described here.

The sum of these factors leads to the sixth quantity. This is important for the functioning of the interplay of the first five.

It is necessary here to go somewhat further because physical laws in connection with the flow are important here for assessing the prevailing forces:

The cause of a flow is regarded from the physical viewpoint as always being a pressure difference $\Delta p$ on a section of a pipe system. Although a pipe system in the narrower sense is not present in our case, the tissue through which flow is to take place can be regarded as a closed system through which the wound discharge must seek its own routes and channels. In this context, it is subject to retarding influences such as shear forces, resistances to flow, frictional conditions, mechanical pressure differences, tangential stresses, forces of currents, changing diameters of the routes and channels and other influencing quantities. Despite the slow flow thereof, the conditions for characterization as laminar flow are not present; on the other hand, the condition of higher flow rate for characterization as turbulent flow is not present either.

On the assumption that the Reynolds number Re, an empirical number which describes approximately a ratio between impulses and possible springing due to friction, is below the change-over limit of 2300, it would be obvious to suppose that the conditions are rather of laminar flow in the case of untreated ulcers of the described origin.

Constant laws on the direction of flow and on the flow rate are certainly not available; on the contrary, mixtures of different laws such as the Hagen-Poiseuille law or the Bernoulli law or the influence of the Fåhraeus-Lindquist effect (influence of the vessel diameter, axial migration) are to be found.

Subsequent to this rather purely physical consideration of flow conditions, it is important that a wide variety of phases, conditions, pressures and flow rates exist in the untreated wound region.

Following this, the above five forces come together. This is because the osmotic potential of a superabsorbent breaks through this disorder and creates a direction of flow of the wound fluid by sucking it to the surface and also aspirating fluids in the depth of the wound through the sum of the forces mentioned. The impulse on the first water molecules into the dressing generates an impulse for all the following water molecules since they are held together in the form of a chain by the forces mentioned or else by "van der Waals forces". The pull on the first member creates a pull on the last member and, in a sense of an automatic, dynamic continuation of these processes, the water molecules permanently follow the flow once it has been set up, because the osmotic gradient of the superabsorbent creates a one-way street into the product.

The gradient of osmotic force and cohesion leads to dehydration in the depth of the tissue, directly in the spatial vicinity of the insufficient vein. The dressing applied to the wound surface fulfils its primary function in precisely this depth of the tissue and removes the water there and dehydrogenates the oedema. For this purpose, it acts through the tissue located between floor of the wound and bottom of the wound and performs transtissual aspiration of perivenous hyperhydrations without being in particular spatial proximity thereto. The high osmotic potential removes the non-superficial oedemas from the wound. In a gentle and mild manner, especially without dehydrogenating cells or air, the extent of the flow of exudate through these channels regulates the suction force through the product actively starting with large amounts of exudate, and turning towards the surface of the floor of the wound even more, whereas with small amounts only atmospheric moisture is acquired by vaporization processes. The principles of moist therapy are also afforded and assisted in all cases.

The result is a suction dressing which actively removes biorelevant noxae such as germs, toxins, proteases etc. gently in the understanding of the under high osmotic pressure. In this case, the pathological exudate is to be regarded less as a problem which needs to be overcome and is injurious to wound healing but, on the contrary, it becomes an item which is conducive to healing: it forms the transport medium for this cleansing suction effect and, after entry into the dressing, is returned to the wound as atmospheric moisture after it has been freed of its harmful substances, because they remain in the dressing and do not evaporate. The dressing thus cleanses parts of the exudate after this has carried its own and other harmful materials into the dressing.

It has found the route into the dressing because it was stimulated to flow in a predefined direction. This dynamization of water which tends to be static in a region which is accessible only by surgery and in the spaces between cells leads to the formation of flow channels and thus to relief of the perivenous tissue. During this process, the pathological exudate becomes a solution for rinsing the wound surface and the depth of the wound and, through the continuous flow, keeps the flow channels open.

As a difference from vacuum therapy, the maximum suction efficiency is reduced locally and successively during the use and is therefore not static in the same way as an electronically adjusted pump pressure and is also less hazardous. The required suction force of the dressing, which is achieved through the superabsorbents, is reduced from the extent of the exudation which is present on a proportion of the area, and is thus determined, so that it is possible to speak here of a wound-adapted control of suction force. Depending on the phase of wound healing and the condition of each square centimeter of a wound, a suction efficiency which is typical of the respective wound situation arises.

An additional circumstance is that, in contrast to vacuum therapy, the dressing eliminates the germs which have been rinsed out and the possibly infectious exudate immediately after emergence from the depth of the body, and controls the germs directly after flowing into the dressing. The exudate is not discharged and thus does not endanger the staff. It is possible in some cases for endemically or epidemically relevant germs to be disposed of only as expensive and costly infectious liquid material.

It is important in this context that the desired effect requires of a pressure of at least about 20 mm Hg, because the suction is insufficient below these values in most cases. The direct proximity of the carrier of the osmotic potential, which is created by the thin covering for the floor of the wound produces this subatmospheric pressure.

This also reveals another significant difference from other dressing materials. This is because when these dressings comprising in particular cellulose wadding, fluff pulp or nonwoven come into contact with exudates they directly lose their structural integrity and degenerate when thoroughly moistened. Very soon after making contact with exudate, this dressing is wet and no longer has any suction and tractive force. In view of the need to aspirate in the depth of the tissue, the suitability of such a dressing as dressing material for a venous leg ulcer is in doubt. When disorders of this type are treated with modern, hydroactive dressings such as polyurethane foams, it becomes evident that the progress made is still inadequate.

Exudate and germs form the intended breaking point of the healing. Exudate maintains germs, and germs lead to exudate. Oedemas lead to a diminished immune response, and the cycle is completed. If this course is interrupted, the wound heals and closes.

This idea takes account in particular of the fact that wounds are not homogeneous and the same at every point. Many wounds experience all phases of wound healing at the same time by being necrotic and dead in one place, infected and coated at another, exuding and watery at one place, fibrinous at another and hypergranulating at yet another. The edge of the wound is in one place, inflammation at another, freshly epithelialized tissue at one place and a bleeding lesion at another owing to the painful removal of adherent dressings.

Automatic adaptation to the respective conditions takes place with the dressing described herein because it is appropriate for each of the wound situations mentioned by providing the appropriate response at every point. Necrotic regions are softened by it by atmospheric humidity and scoured, germs are absorbed by it together with the exudate from the regional inflammation, deposits are concentrated on the outer wall of the covering and are removed when the dressing is removed, watery exudation is removed with high retaining power, hypergranulation is retarded by the dressing through its own weight and the weight of the absorbed exudation, fresh epithelium protects it from exudate and adhesions do not take place, and if they do it is possible to use a commercially available wound-distance lattice as primary dressing.

All typical advantages are also optimized by the dressing having full-area contact with the wound. It must be taken into account here that the surface of a wound is not smooth like a pane of glass but, on the contrary, has an extremely inhomogeneous morphology. From the perspective of a small cell, comparison with an aerial photograph of Germany is perfectly appropriate: mountains in the south, a rather flat area at the top, many high buildings in highly populated areas, and many lakes elsewhere, and possibly even one place below sea level. The realization that scarcely any wound shows only a single phase of healing and healing situation leads to the need for a dressing which treats several phases appropriately at the same time. This may be said to be ensured by the chosen technical approach.

It may be advisable to use one of the foam dressings mentioned as primary full-area contact layer, as long as the advantages of the absorbent article are additionally used. This might take place by the foam being in contact with the wound, and the absorbent article being in direct contact with it on its reverse side in order on the one hand to ensure adaptation to a very inhomogeneous morphology of the floor of the wound via a foam which, as flow-through and contact article, guides the wound fluids directly into the absorbent article. Fulfilment of this function by means of alginates, carbon dressings or cotton materials and nonwovens is also conceivable.

If polyurethane foams are used, they are prone to roll up at the edges. The use of the absorbent article on the reverse side forms a desired mechanistic counter-pressure here and thus contributes to maintaining a full-area contact area.

The external shape of the dressing may be in the form of squares or other geometries, but may also have anatomical shapes such as glove for the treatment of extremities for example.

It is of central importance in all cases that a new understanding of wound treatment, oedema therapy and treatment of vascular insufficiency results through water expelled from veins, oedemas and their fluids being dynamized and guided to the skin surface in order to be removed effectively there so that the wound can close. Destressing, deswelling, deflooding and removal of harmful substances lead to pacification, depth relief and decongestion of tissue, which is cleansed by this rinsing process from the deep perivenous tissue as far as the floor of the wound.

This new understanding includes the possibility of being combinable with vacuum therapy in order to achieve an enhancement of the suction efficiency. Modulations made possible by reducing the air suction efficiency, because osmotic suction efficiencies are added thereto, and therefore allow regulations of the synergistic factors, are conceivable.

In all cases, with and without vacuum, exudation and soiling which have been carried by the rinsing efficiency into the absorbent article is collected in the article.

Synergistic factors may also be interdependent, for example in cases where, for example, exudation is stimulated and increased by surfactants, use of the absorbent article is necessary in order to control the exudation induced.

Other additions may also be natural substances, for example extracts of fruits or nuts; mention may be made here in particular of saponins, extracts of soapnuts: fruits of the soapnut tree (*Sapindus mukorossi*).

The swelling substances may lead via ion exchange processes to reductions in the germ count in the wound region by preventing depolarizations and conduction thereof, or reducing concentration gradients at the cell membrane of organisms or germs. Control of resistant germs may play an endemic or epidemic role here, since the colonized wound often maintains the germ and the germ often maintains the wound. Interruption thereof is a noteworthy measure in inhibiting spread of the germs and their infections.

The possibility of incorporating the superabsorbent granules in a bed of cut and bent cellulose fibres before they swell plays a noteworthy function in the generation of the atmospheric moisture in the wound region, because the surface area is maximized thereby. Cover layers of cellulose, high surface-area granules and intensive surface-area fibres lead overall to a large space and large area for evaporation of absorbed liquid portions and thus for generating and maintaining the desired moist wound milieu.

This type of inner layer as superabsorbent carrier is possible in particular in the case of an airlaid mat.

Non-systemic, local, but necessary dehydration is therefore carried out by a dressing which is avid for exudate and is provided with high osmotic potency. This is because it is not possible to see that a vein is not healthy, and skin and connective tissue die solely for this reason.

It is conceivable only by these rinsing processes to convey impurities, residues of germs, cell detritus, metabolic products of bacteria and cells present in the wound region to the surface in order for them to be directly absorbed and removed in controlled fashion there.

It is advantageous that, besides excess wound fluids, there is also removal of substances which are harmful to wound healing and are present therein, and they may show a shorter residence time in the patient's tissue. The sequelae of pathological processes can be reduced.

The inner layer preferably has more than 40% osmotically active substances based on the total weight. Osmotically active substances may also be present in the covering.

The osmotically active substances may be in powder or granule form, and the granule form may have both the regular spherical or prismatic and irregular shapes such as the shape of a grain of sand.

The inner layer can be designed to absorb fluids whose specific gravity corresponds approximately to that of water, i.e. a value of 1.00, or slightly exceeds the said specific gravity and is about 1.020, it likewise being possible to design for more viscous fluids whose specific gravity may reach for example a value of 3.00.

The osmotically active substances include in particular so-called superabsorbents, but the inner layer may additionally include other osmotically active substances such as salts, sugars, proteins, electrolytes etc.

The aforementioned osmotically active substances may also be a constituent of the covering. The covering may additionally include antimicrobial, odour-inhibiting, disinfecting, fungicidal or other wound healing-promoting substances such as drugs.

The stated concentration of the osmotically active substances utilizing adhesive or cohesive forces of water contributes to regulating hyperhydrations in deeper healthy or pathological tissue not located at the wound surface. The osmotically active pressure gradients are essentially achieved by ion exchange processes.

Oversizing of swelling materials, including in particular superabsorbent particles, contributes to the wound exudate, and solid particles and germs, also being able to be taken out of the bottom of the wound.

The composition of the absorbent article influences, via concentration gradients and differences compared with the wound area, the direction of flow of wound fluids. The suction which is generated by the absorbent article and increases in the direction of the skin surface channels the wound fluids, increases the rate of transport thereof and leads to local immobilization of tissue- and growth-impairing proteases and factors on the inner layer and, in this way, more effectively protects the wound tissue, the tissue of the wound edge and the wound region.

The potency of the osmotically active substance can be chosen so that the extent of a local hydrostatic pressure increase occurs owing to an increased permeability of the vessels is opposed by an effective osmotic pressure gradient which regulates the hyperhydration situation of the tissue between the two opposing centres by defined direction of flow and flow rate, so that functionally the sum of hydrostatic superatmospheric pressure and osmotic suction leads to a smaller collection of fluid in the interstitial space. The osmotic potency of the absorbent article can also regulate cellular hyperhydrations.

The potency of the osmotically active substance of the absorbent article can be chosen so that the extent of a local capillary hypertonicity is opposed by a proportional osmotic suction effect which curtails the persistence of fluid in nonphysiological amount in the direction of physiological hydration.

The inner layer or the covering may furthermore serve as depot for medicaments or solutions which can be delivered continuously to the wound region.

The inner layer can consist of a blend of superabsorbent polymers with cellulose as carrier material, and two two-dimensional cover layers. In this context, at least one of the cover layers can consist of cellulose, it being possible for the bulk density of the cover layer to differ from that of the carrier material.

The inner layer may have admixtures prepared on the basis of acrylic acid or on the basis of activated carbon.

The absorption capacity of the absorbent article may be above a value which is about 95 g of water/100 $cm^3$ of the absorbent article measured as specified in DIN EN ISO 53923.

The absorbent article may comprise in at least one location starch polymers because these show a particularly hydrophilic character. Starch polymers which can be employed are for example native starch polymers based on maize, potatoes or rice and having a high moisture sensitivity.

The absorbent article may be coolable and, at least partly presaturated with fluids, be placeable in frozen form on acute wounds, sutures or other areas of skin. The fluid may be antimicrobially active fluids, hyaluronic acid or other substances which promote the wound-healing process, such as quaternary ammonium salts.

The absorbent article can be placeable on body surfaces which have an applied electric field. Direct current is preferred in this context in particular.

It is also possible to add microbial substances resulting from fermentation processes.

One of the active substances may be a substance which promotes the formation of molecular networks. This may be based in particular on hydrophilic processes if linkages to water molecules are produced and the storing articles have crosslinkings.

The technical approaches of the hydrophilic processes may be based on fundamental physical processes such as the tendency to balance and harmony. Entropically driven processes, enthalpy, Brownian motion of molecules, as well as the utilization of dilution tendencies may have priority. The reduction of electrostatic interactions may also have priority.

The absorbent article may comprise a substance which is surrounded partly or entirely by at least partly liquid-permeable silicone shells. For this purpose, a mat of the airlaid type which includes carboxymethylcellulose (CMC), not pure cellulose, as carrier material for superabsorbent particles, may be present. Here, for example a mixture of superabsorbent particles with carboxymethylcellulose is subject to possible covering with a thin cellulose layer; this covering may be present on a plurality of areas or be entirely absent. This embodiment is particularly favourable because the cellulose incorporated in the classical mat is greatly compressed and may give a hard and injurious impression, whereas the carboxymethylcellulose fibres possibly remain softer. Further substances such as alginates or other substances mentioned herein may be added instead or mixed with these fibres. The swelling process may partly pass through any shells and have direct contact with the wound surface.

Inhomogeneous carrier substances for superabsorbent particles may be present in at least one layer of the absorbent article in order to give the layer or the mat not only the storage function but additionally to carry out further functions such as temperature maintenance, adaptation to the floor of the wound or germ reduction. It is possible here to combine for example silver preparations or polyhexanide and activated carbon. The polyhexanides may be present in dried form, liquid or bound to parts of the absorbent article.

The absorbent article can be introducible into body orifices, creases, elevations or other cavities of the patient's body, where it can be employed in particular for healing ulcers and tissue substance defects, for example in the case of dental surgery procedures in the mouth.

The inner layer may be 3% to 90% smaller in area than the covering, where the area of the covering is that limited by the surrounding seam.

The covering preferably consists of a woven or nonwoven which weighs at least 20 grams per $m^2$. The covering can be formed from synthetic fibres which are woven or assembled in a nonwoven manner, such as polypropylene or polyethylene fibres, of natural fibres or a mixture of natural and synthetic fibres. The covering may be permeable both for liquid and for viscous substances.

The covering can consist of a folded or of two sheets which are joined together on their periphery, the joining of the sheets with one another being produced by ultrasound, bonding, sewing or similar thermal, physical or chemical processes. The covering may furthermore have soft edges on its periphery which results for example from the covering material extending beyond the seam area.

The covering may have pores or meshes which are in each case smaller than the dimensions of the substances to be absorbed in granule or powder form. The pores or meshes may also be larger, preferably slightly larger, than the superabsorbent particles when the latter are embedded in the carrier material of the inner layer, or are present in a—from the use of the absorbent article—dried adhesive dispersion therein.

The covering has various functions in this context. Although a technically not too elaborate polypropylene nonwoven can be chosen, it fulfils many functions by allowing water vapour to pass through to the outside after it has allowed it to enter the absorbent article as liquid exudate. To avoid ingrowth of tissue and vessels, it has perforations or pores whose size is chosen so that the granulation tissue of the wound, especially at the edge of the wound, cannot grow into the covering. For example, the perforations or pores present on the periphery of the covering may be smaller than those of the remaining region of the covering.

The covering may be fabricated from natural materials such as cotton or silk fabric, or from perforated synthetic sheet or from synthetic fabric. The covering surrounding the mat can be produced partly or wholly from a so-called wound-distance lattice, with the alignment of its smooth or rough side being dependent on the particular purpose. The smooth side protects the wound from irritation and unwanted influences of a secondary dressing. A rough surface by contrast appears to be active in moving on the wound and brings about a desired chemotactic stimulus on formation of new tissue.

The covering with mat accommodated therein, and the foam material layer, can be disposed within an outer fluid-permeable covering.

Finally, the covering material can be designed to be adhesive so that viscous, tacky, crosslinked or corpuscular substances adhere to the covering and are conveyed out of the wound when the absorbent article is changed.

The absorbent article according to the invention can be used universally for different wound therapies (leg ulcer, incised wounds, abrasions, inflammatory wounds, burns etc.), wound-healing phases and for use in collecting devices such as drain, stoma, fistula or other collecting bags.

Some selected possible uses are listed below:

- as dressing for the treatment of an oedematous or inflammatorily altered wound region;
- as dressing for the treatment of a microbially affected wound surface by guiding, by the suction force, germs or cell detritus with enclosed, dehydrogenated or into anaerobic areas of the swollen absorbent article;
- as dressing for removing inflammatory cytokines, metrix metallo proteases, TIMPs, degraded fibronectin (draws the tissue together) or other chronifying substances;
- as dressing material for combination with sponge-like, for example open-pore wound-treatment means;
- as dressing for regulating the atmospheric moisture, because the absorbent article discharges the aqueous constituents via the vapour pressure thereof into the air again;
- as dressing over an initially applied wound-distance lattice or a gauze as secondary dressing without direct two-dimensional contact with the wound;
- as dressing underneath a water-impermeable film which immobilizes the absorbent article on the patient;
- as dressing underneath a water vapour-permeable film to achieve a breathable dressing;
- as dressing for chronic venous insufficiency (CVI) with secondarily weeping wound for compression via the swelling process of the leak from the affected vessel;
- as input into a wound treatment which includes at least temporarily subatmospheric air pressure conditions.

Figure 1B:
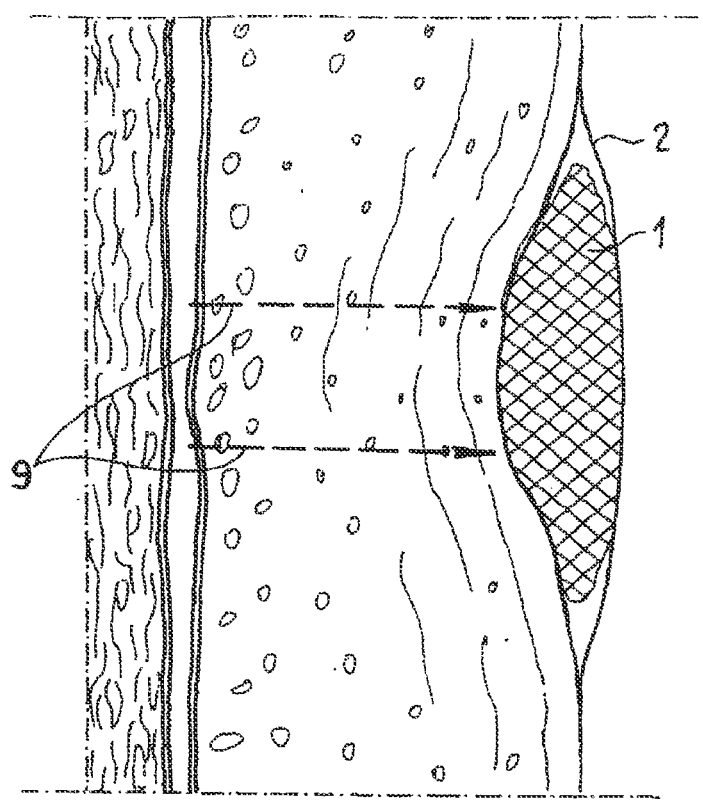

FIGS. 1*a* and 1*b* show diagrammatically an absorbent article 100 in section, consisting of a liquid-absorbing inner layer 1 and of a liquid-permeable perforated covering 2. The inner layer 1 is composed of a cellulose-like carrier material 3 and two two-dimensional, likewise cellulose-like cover layers 4.1, 4.2, with only the core, i.e. the carrier material 3, being permeated with osmotically active superabsorbent polymers in the form of superabsorbent particles 20. The cover layers 4.1, 4.2 are joined to the carrier material 3 without adhesion, i.e. the flat joining together took place by compressive force.

The covering 2 formed from polypropylene fibres has two congruent liquid-permeable rectangular sheets 2.1, 2.2 which are joined together at their edges by an ultrasonic seam 6 to form a pocket so that the layer 1 located inside the pocket formed by the covering occupies, in the non-wet state, an area which is limited by the seam and corresponds to about 75% of the area of the sheet 2.1, 2.2 (cf. FIG. 1a). The covering 2 additionally has on its periphery soft edges 7 which result from covering material extending beyond the seam area.

Although the cellulose-like material of the inner layer 1 is liquid-absorbing, satisfactory results are obtained only by an empirically established blending of this material with superabsorbent particles 20. Accordingly, the nonwoven-like carrier material 3 has been filled, laid and prepared in such a way that it had, together with the superabsorbent particles 20 which are present therein and are in powder and granule form, a mass per unit area of about 430 g/m$^2$, with the proportion of superabsorbent particles 20 in the carrier material 3 being 54% by weight.

As depicted in FIG. 1b, the absorbent article 100 which is firstly placed in the dry state on a wound (leg ulcer) in the wound bed is swollen after direct wetting with the wound fluid. An interaction with the wound bed takes place, via the function of absorbing wound fluid, since the absorbent article 100 stores the wound exudate, releases vaporized water, exchanges ions and thereby reaches a weight which controls the extent of the granulation in the wound bed.

The absorbent article separates the wound exudate entering it and releases parts thereof to maximize its surface area (droplets of atmospheric moisture). The inner layer 1 changes its thickness in accordance with the local suction conditions caused by the osmotic pressure.

Figure 2:
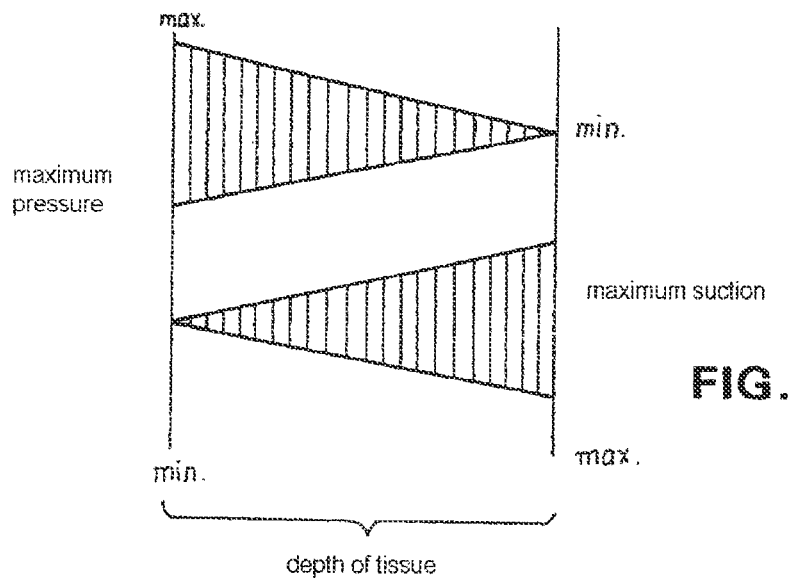
FIG. 2 pressure and suction diagrams relating to the wound situation shown in FIG. 1.

FIG. 2 shows pressure and suction diagrams corresponding approximately to the wound situation shown in FIG. 1b. The pressure is a maximum in the vein region 10 and decreases in the direction of the wound. The suction is in turn a minimum in the vein region and increases to its maximum in the wound region. The suction arrows 9 show the channelled direction of flow of the wound exudate.

The absorbed liquid does not flow back. The used, swollen absorbent article 100 can be disposed of with adherent particles.

Figure 3:
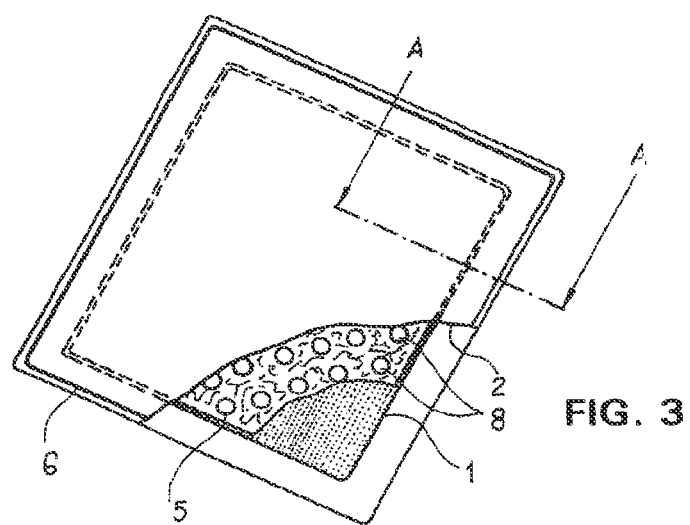
FIG. 3 a second absorbent article according to the invention with an additional inner layer, in a perspective view.
Figure 4:
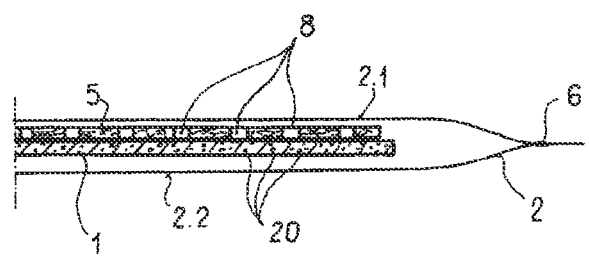
FIG. 4 a section A-A as shown in FIG. 3.

FIGS. 3 and 4 show a two-layer absorbent article 200 in which the covering 2 surrounds, apart from the first layer 1 which is shown in FIG. 1a and is permeated with superabsorbent particles 20, also an additional layer 5 consisting of carboxymethylcellulose fibres. Since the absorbent article 200 with the layer 5 can be placed on the respective wound, a plurality of continuous apertures 8 are provided on the layer 5 and make it possible for wound fluids to be transported in the direction of the second, cellulose-like layer 1. The apertures 8 have a diameter of about 3 to 4 mm.

Figure 5:
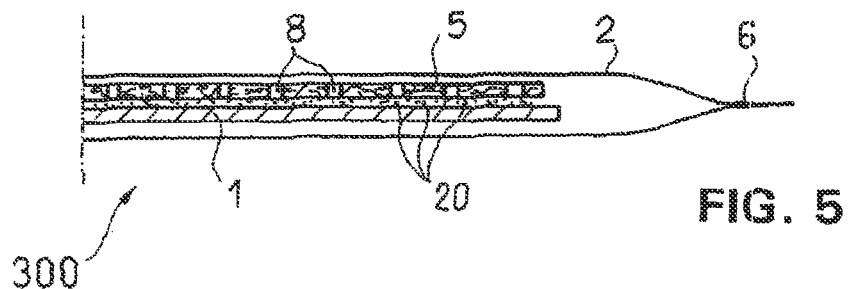
FIG. 5 another absorbent article with two inner layers, in a diagrammatic section.

An embodiment differing somewhat from that in FIG. 4 is depicted (absorbent article 300) in FIG. 5. The superabsorbent particles 20 are distributed in a medically acceptable, dried adhesive dispersion, which dissolves after moistening with the wound exudate, between the two inner layers 1 and 5. The adhesive dispersion may optionally be supplemented with aforementioned substances promoting wound healing.

Figure 6:
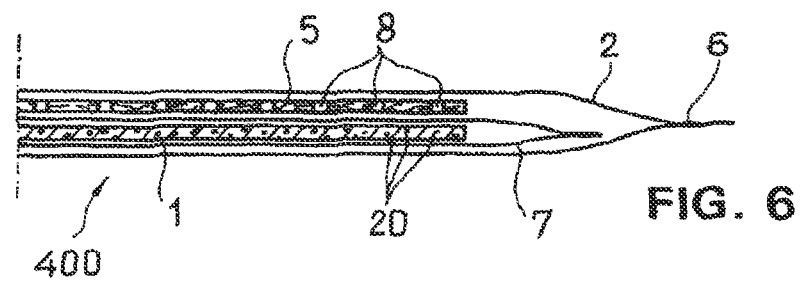
FIG. 6 an absorbent article having an additional inner covering, in a diagrammatic section.

Furthermore, FIG. 6 shows an absorbent article 400 which, apart from the covering 2, also includes a second, inner covering 7. The two coverings 2; 7 are liquid-permeable. The perforated layer 5, which consists of carboxymethylcellulose fibres, lies between the inner covering 7 and an inner surface 9 of the outer covering 2. The inner covering 7 surrounds the first layer 1 which is permeated by superabsorbent particles 20. The absorbent article 400 can likewise be placed with its perforated layer 5 directly on the wound.

Figure 7:
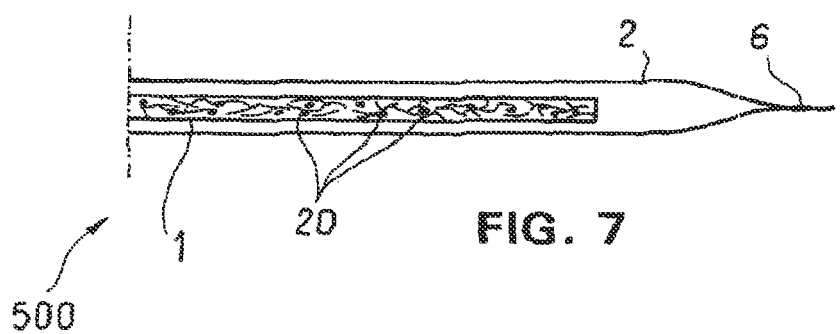
FIG. 7 a further absorbent article having a hydrophilic inner layer made of carboxymethylcellulose, likewise in a diagrammatic section.

Finally, FIG. 7 shows an absorbent article 500 consisting of the liquid-permeable covering 2 and a hydrophilic inner layer 1 composed of carboxymethylcellulose 1, which is additionally permeated with superabsorbent particles 20. The covering 2 consists of a perforated wound-sparing film material which is obtainable on the market for example under the brand name Tredegar and which can be employed for producing so-called wound-distance lattice. Optionally, the inner layer 1 can be perforated and, where appropriate, provided with at least one cover layer as has been described for FIG. 1a.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. An absorbent article for application to human or animal skin surfaces in a region of a wound, the absorbent article comprising:
    an outer covering comprising two layers which are liquid-permeable and which are joined together to form a pocket, said pocket being permeable to liquid substances; and
    an inner layer in a form of a mat, said mat being located within said pocket and being freely movable within said pocket;
    wherein the inner layer surrounded by the outer covering consists essentially of a mixture of an amount of strongly osmotically active substances which are superabsorbent particles of crosslinked, partially neutralized acrylic acid polymers, with an amount of osmotically weak or osmotically inactive substances, and
    wherein more than 40% by weight of the mat comprises said osmotically active substances and is capable of functioning as a dressing for inhibition of harmful proteases.

2. The absorbent article according to claim 1, wherein the inner layer is formed from an intermediate layer consisting of a mixture of superabsorbent polymers with cellulose as carrier material, and of two two-dimensional cover layers, or consists of hydrophilic fibers, and superabsorbent polymers with or without cellulose.

3. The absorbent article of claim 2, wherein the hydrophilic fibers are carboxymethylcellulose fibers.

4. The absorbent article according to claim 1, wherein inhibition of harmful proteases is inhibition by removing, absorbing and/or fixating harmful proteases.

5. The absorbent article according to claim 1, wherein the harmful proteases are selected from a group consisting of matrix metallo proteases (MMPs) and tissue inhibitors of metallo proteases (TIMPs).

6. The absorbent article according to claim 1, wherein the inner layer has a mass per unit area of at least 300 g/m$^2$, with the mass per unit area of the proportion of osmotically active substances which is uniformly dispersed therein being at least 100 g/m$^2$.

7. The absorbent article according to claim 1, wherein the inner layer includes one or more osmotically active substances selected from a group consisting of salts, types of sugars, proteins and electrolytes.

8. The absorbent article according to claim 1, wherein the inner layer leads to local immobilization of tissue-impairing proteases and growth-impairing proteases and factors transported by the wound exudate.

9. The absorbent article according to claim 1, wherein the absorption capacity of the absorbent article is above a value which is about 95 g of water/100 cm$^3$ of the absorbent article measured as specified in DIN EN ISO 53923.

10. The absorbent article according to claim 1, wherein the outer covering is adhesive for viscous, tacky, crosslinked or corpuscular substances which can thus be conveyed out of the wound when the absorbed article is changed.

11. The absorbent article according to claim 1, wherein the inner layer is configured such that absorbed liquid is only released if the inner layer becomes completely saturated.

12. A method of treating harmful proteases in human or animal skin surfaces in a region of a wound, the method comprising steps of:
   administering an absorbent article of claim 1 in a form of a dressing to the wound of a subject; and
   inhibiting harmful proteases with the dressing.

13. The method of claim 12, wherein the inner layer is formed from an intermediate layer consisting of a mixture of superabsorbent polymers with cellulose as carrier material, and of two two-dimensional cover layers, or consists of hydrophilic fibers, and superabsorbent polymers with or without cellulose.

14. The method of claim 13, wherein the hydrophilic fibers are carboxymethylcellulose fibers.

15. The method according to claim 12, wherein the step of inhibiting harmful proteases further comprises inhibiting at least one of matrix metallo proteases (MMPs) and tissue inhibitors of metallo proteases (TIMPs).

16. The method of claim 12, wherein the inhibition of the harmful proteases is an inhibition by removing, absorbing and/or fixating harmful proteases.

17. The method of claim 12, wherein the inner layer has a mass per unit area of at least 300 g/m$^2$, with the mass per unit area of the proportion of osmotically active substances which is uniformly dispersed therein being at least 100 g/m$^2$.

18. The method of claim 12, wherein the outer covering has pores or meshes which are smaller than dimensions of substances to be absorbed in granule or powder form.

19. The method of claim 12, wherein the inner layer leads to local immobilization of tissue-impairing proteases and growth-impairing proteases and factors transported by the wound exudate.

20. The method of according to claim 12, wherein at least one detergent is added to the region of the wound as adjacent dressing material, which detergent brings about an increase in exudation of the wound.

* * * * *